United States Patent
Ward et al.

(10) Patent No.: US 10,932,505 B1
(45) Date of Patent: Mar. 2, 2021

(54) ENZYME-ENHANCED ANTI-VIRAL FABRICS

(71) Applicants: Mandy Jane Ward, Los Osos, CA (US); Adam Warwick Bell, San Francisco, CA (US)

(72) Inventors: Mandy Jane Ward, Los Osos, CA (US); Adam Warwick Bell, San Francisco, CA (US)

(*) Notice: Subject to any disclaimer, the term of this patent is extended or adjusted under 35 U.S.C. 154(b) by 0 days.

(21) Appl. No.: 17/022,236

(22) Filed: Sep. 16, 2020

Related U.S. Application Data

(60) Provisional application No. 63/076,404, filed on Sep. 10, 2020.

(51) Int. Cl.
| | | |
|---|---|---|
| *A41D 13/11* | (2006.01) | |
| *D06M 17/00* | (2006.01) | |
| *B01D 39/08* | (2006.01) | |
| *D06M 16/00* | (2006.01) | |
| *A61K 38/46* | (2006.01) | |
| *A61K 38/43* | (2006.01) | |
| *A61P 31/12* | (2006.01) | |

(52) U.S. Cl.
CPC .......... *A41D 13/1192* (2013.01); *A61K 38/43* (2013.01); *A61K 38/465* (2013.01); *A61P 31/12* (2018.01); *C12Y 301/01003* (2013.01); *C12Y 304/00* (2013.01); *D06M 16/003* (2013.01)

(58) Field of Classification Search
CPC ... A41D 13/11; A41D 13/1192; D06M 17/00; B01D 39/08
See application file for complete search history.

(56) References Cited

FOREIGN PATENT DOCUMENTS

WO 067873 * 6/2010

* cited by examiner

*Primary Examiner* — Maryam Monshipouri
(74) *Attorney, Agent, or Firm* — Adam Warwick Bell

(57) ABSTRACT

The invention provides fabrics that incorporate enzymes that inactivate microbial pathogens, particularly enveloped viral particles such as those of Influenza virus and Coronavirus such as Covid-19. The fabrics of the invention may be used in the production of various items including protective facemasks.

6 Claims, 7 Drawing Sheets

| Trade Names | Source organism | Manufacturer |
|---|---|---|
| Alkaline proteases: subtilisins | | |
| Alcalase | Bacillus lichenformis | Novo Nordisk, Denmark |
| Savinase | Alkalophilic Bacillus sp. | Novo Nordisk, Denmark |
| Esperase | Alkalophilic Bacillus sp. | Novo Nordisk, Denmark |
| Liquanase | | Novo Nordisk, Denmark |
| Everlase | | Novo Nordisk, Denmark |
| Ovozyme | | Novo Nordisk, Denmark |
| Polarzyme | | Novo Nordisk, Denmark |
| Maxacal | Alkalophilic Bacillus sp. | Gist-brocades, Delft, The Netherlands |
| Maxatase | Alkalophilic Bacillus sp. | Gist-brocades, Delft, The Netherlands |
| Opticlean | Alkalophilic Bacillus sp. | Solvay Enzymes GmbH, Hannover, Germany |
| Optimase | Alkalophilic Bacillus sp. | Solvay Germany |
| Protosol | Alkalophilic Bacillus sp. | Advanced Biochemicals Ltd., Thane, India |
| Alkaline protease "Wuxi" | Alkalophilic Bacillus sp. | Wuxi Synder Bioproducers Ltd., China |
| Proleather | Alkalophilic Bacillus sp. | Amano Pharmaceuticals Ltd., Nagoya, Japan |
| Protease P | Aspergillus sp. | Amano, Japan |
| Durazym | Protein engineered variant of Savinase | Novo Nordisk, Denmark |
| Maxapem | Bleach-resistant, protein engineered variant of alkalophilic Bacillus sp. | Solvay, Germany |
| Puralact | Recombinant enzyme donor Bacillus lentus Expressed in Bacillus sp. | Genencor International Inc., Rochester, USA |
| Amylases | | |
| BAN | Bacillus amyloliquefaciens Recombinant enzyme | Novo Nordisk, Denmark |
| Termamyl | Donor- Humicola sp. Expressed in Aspergillus sp. | Novo Nordisk, Denmark |
| Stainzyme | | Novo Nordisk, Denmark |
| Duramyl | | Novo Nordisk, Denmark |
| Maxamyl | Alkalophilic Bacillus sp. | Gist-brocades, Delft, The Netherlands |
| Solvay amylase | Thermostable Bacillus lichenformis | Solvay, Germany |
| Lipases | | |
| Lipolase | Recombinant enzyme Donor- Humicola lanuginosa Expressed in Aspergillus oryzae | Novo Nordisk, Denmark |
| Lumafast | Recombinant enzyme Donor- Pseudomonas mendocina Expressed in Bacillus sp. | Genencor, USA |
| Lipofast | NA | Advanced Biochemicals, India |
| Cellulases | | |
| Celluzyme | Humicola insolens | Novo Nordisk, Denmark |
| Endolase | | Novo Nordisk, Denmark |
| Mannanase | | |
| Mannaway | | Novo Nordisk, Denmark |
| (Novozyme report, 2006; Kumar et al., 1998). | | |

ENZYME-ENHANCED ANTI-VIRAL FABRICS

PRIORITY

This application claims priority to and the benefit of U.S. provisional application 63/076,404 filed 10 Sep. 2020.

FIELD OF THE INVENTION

The embodiments of the present invention relate to enzyme-impregnated fabrics that inactivate pathogenic microbes including viral particles such as enveloped viral particles (FIG. 1) including Covid-19 and Influenza virus. The fabrics of the invention may be used in the production of disposable surgical gowns and head coverings, clothes, bedding, filters and protective facemasks.

BACKGROUND

Many human illnesses are transmitted from one individual to another by aerosols or fomites.

The 1918 Spanish flu pandemic was caused by an H1N1 influenza virus. It infected 500 million people around the world (about 27% of the then world population) and is estimated to have killed about 60 million people. Annual flu epidemics result in a yearly average of about 65,000 deaths globally.

Severe acute respiratory syndrome (SARS) was caused by the SARS coronavirus (SARS-CoV), and between November 2002 and July 2003, an outbreak in China caused about 8,098 cases and 774 deaths (9.6% fatality rate).

COVID-19 first emerged in Wuhan, Hubei, China and is the cause of the present 2019-20 coronavirus pandemic. Its effect and severity is yet to be determined. The novel coronavirus is a positive-sense single-stranded RNA virus, same as the SARS and MERS virus.

The person-to-person transmission of influenza virus, especially in the event of a pandemic caused by a highly virulent strain of influenza, such as H5N1 avian influenza, is of great concern due to widespread mortality and morbidity. Because airborne transmission is key, public health interventions should focus on preventing or interrupting this process.

Typical face-masks are uncomfortable and only partially effective. Fitting is usually sub-optimal leaving air-gaps which have a much lower air resistance for inhaled air than the fabric of the mask, and which are therefore the path of least resistance for inhaled air. Pathogens entering the mask may consequently be inhaled. Breathing soon becomes tiresome due to inherent air resistance through the fabric. Air resistance and discomfort leads to frequent desire to remove or adjust the mask. The present invention addresses all these aspects.

Respirators (N95 and N100; both commercially available) are masks designed to shield the wearer from inhalational hazards, as opposed to surgical masks, which are designed to protect others from contaminants generated by the wearer. Both are difficult to use effectively because of discomfort, poor fitting and movement and entrance of air around the sides of the mask.

One major problem with masks and respirators is that in order to filter out very small particles, the air has to pass through dense filters with considerable air resistance. This makes them more uncomfortable to wear and difficult to use, meaning that as the weave of the material becomes tighter and the effectiveness of the filter increases, wearing compliance decreases, particularly in the general public. Also, because the air has to pass through an area of high resistance, the air is likely to try to find the path of least resistance and to find an unfiltered pathway, if such exists, letting in unfiltered air from the outside. This happens even if the filter has a large surface area. The invention overcomes this problem by providing sterilization of air moving through each potential pathway.

A universal issue with masks is correct fit. Because the air has to pass through an area of high resistance, the air is likely to try to find the path of least resistance and to find an unfiltered pathway, if such exists, letting in unfiltered air from the outside. A related issue is the tendency of mask-wearers to touch, adjust, partially remove or fully remove the mask. Users do this because masks become uncomfortable, hot, moist and itchy. Adjusting the mask reduces any seal effect and allows air to flow directly round the mask into the mouth or nose. Additionally touching the mask transfers the concentrated particles from the outside of the mask to the fingers of the user, increasing the probability of introduction of an infectious dose to the user if they then touch their nose, mouth or eyes. Current masks concentrate particles on their outside, increasing the probability of introduction of an infectious dose to the user if they then touch their nose, mouth or eyes. The reason masks become uncomfortable is due to restricted breathing and trapped humidity within the mask, which makes it itchy and unpleasant. The smaller the pore size, the more air-flow is restricted. Reducing the pore size of disposable facemasks, so that they would remove smaller virus-containing droplets, would impact the ability of the wearer to breathe, encouraging removal or adjustment of the mask. This solution would therefore be counterproductive.

Fabrics with antimicrobial additives are known. These include additives based on silver, copper, and zinc (so called "Organic Antimicrobial Additives") that include phenolic biocides, quaternary ammonium compounds and fungicides (thiabendazole).

Copper and silver-containing anti-microbial facemasks that are currently being produced reduce growth of bacteria and fungi in the mask material, but are not efficient at killing or inactivating a significant proportion of viruses entering or passing through the mask. Any killing effect that is theoretically possible is only provided on contact with the metal, and the vast majority of the surface area of such masks does not incorporate an effective proportion of metal ions. Making these masks anti-viral using this approach would require adding a proportion of metal to the material that would make the mask both extremely uncomfortable to wear and prohibitively expensive. Consequently, this solution is impractical.

There are also masks designed recently by Dibakar Bhattacharyya at the University of Kentucky that incorporate proteolytic enzymes that specifically bind to attach to the spike proteins of the coronavirus and kill the virus. Although this design is theoretically possible, there are several potential difficulties and disadvantages in the design. Firstly, these are enzymes that bind specifically to the spike-protein. These enzymes are not commercially available easily or cheaply or in large quantities. They must be created and manufactured by complex and expensive biological processes. Certainly they are not readily available in 2020 during the present COVID-19 outbreak. This contrasts with the enzymes (proteases and lipases) of the present invention which have been developed over many years for use in washing detergents. They are cheap, well-researched and dermatologically tested. Secondly, the University of Kentucky mask, when in use, will not necessarily create an appropriate chemical and osmotic environment for the proteases to adopt the correct confirmation that will be required for enzyme activity. Thirdly the University of Kentucky (UK) mask only uses specific protease enzymes that bind only to the coronavirus spike protein. It does not employ non-specific enzymes, and it does not comprise lipases or other enzymes or multi-enzyme blends as does the present invention. Fourth, the enzymes used in the UK mask are not and have not been designed to be active at low temperatures, such as at room temperatures, for example 10-20 degrees centigrade. Therefore they will not function efficiently as room temperatures.

There is a long-felt need, with a particular new urgency, for fabrics impregnated with or sprayed with enzymes that inactivate pathogenic microbes including viral particles, particularly enveloped viral particles such as those of Coronavirus (e.g. Covid19) and Influenza virus. The fabrics of the invention may be used in the production of protective facemasks.

SUMMARY OF THE INVENTION

The invention provides fabrics impregnated with or sprayed with enzymes that inactivate pathogenic microbes including viral particles, particularly enveloped viral particles such as those of Coronavirus (e.g. Covid19) and Influenza virus. The fabrics of the invention may be used in the production of protective facemasks.

BRIEF DESCRIPTION OF THE FIGURES

FIG. 2. A non-exclusive table of enzymes used in the fabrics of the invention.

FIG. 7. Schematic diagram showing how activated enzymes disperse into aerosol droplets introduced into the face mask material during breathing (or sneezing, coughing, laughing, etc.)

DETAILED DESCRIPTION OF THE INVENTION

Figure 1:
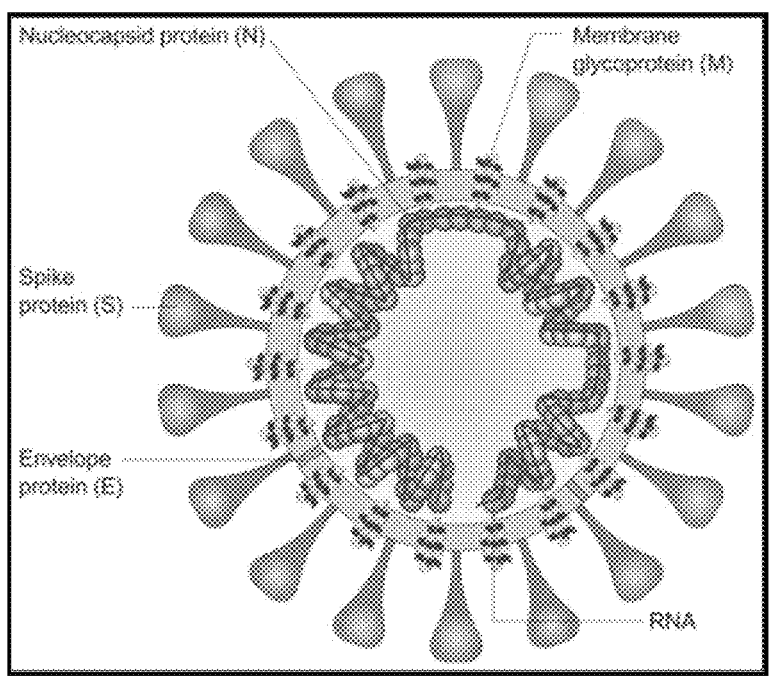
FIG. 1. A schematic diagram of a Coronavirus.

The invention provides fabrics impregnated with or sprayed with enzymes that inactivate viral particles, particularly enveloped viral particles such as those of Coronavirus (e.g. Covid19) and Influenza virus. The fabrics of the invention may be used in the production of protective facemasks.

(I) The Problem Addressed by the Invention

Disposable facemasks being worn by the general public during the Covid-19 pandemic prevent infection both by preventing the wearer from touching their face and by removing virus from their expelled breath (if they are infected), thereby preventing infection of other people. These masks may also prevent some virus from being breathed in by non-infected persons. However, the fabric weave of the material used to make these masks leaves sufficient pore space for small, virus-containing droplets, to pass through. There is therefore a need for the efficiency of these masks, that are based on size-exclusion alone, to be improved.

Some disposable facemasks are marketed as anti-microbial. These masks contain metals, such as silver or copper. However, the addition of metals to these masks does not add significant anti-viral properties. The metals prevent the growth of bacteria and fungi, thereby extending their lifetime. The metals have not been shown to kill virus lodged in the mask material. Adding an efficient anti-viral component to disposable facemasks would improve their efficiency and efficacy in preventing viral infections.

The aim of this invention is to enhance the efficiency and efficacy of disposable facemasks in preventing viral infection by incorporating virus-degrading enzymes into the mask material. The enzymes will degrade virus particles passing through the mask and inactivate virus lodged in the mask material, thereby reducing infections based on wearers transferring virus from their masks to their faces when the mask is worn or touched during removal, repositioning or other touching.

(II) What are the Currently Used Solutions that Address this Problem?

Disposable "surgical" facemasks of the type worn by the public (i.e. non-N95 masks), are meant to filter out virus by size exclusion. While the SARS-CoV-2 virus is 120 nm (0.12 microns) in diameter, such viral particles do not exist in an environmental sense as individual particles, but are carried in water droplets with a range of much larger sizes, of which only the largest are removed by the current "surgical" masks. Reducing the pore size of the masks provides one method of increasing viral filtration efficiency.

N95 masks have a filtering ability down to between 0.3 and 0.1 microns (depending on the manufacturer's claims) and are said to filter out particles with such a diameter with 95% efficiency.

Home-made fabric masks have become popular, but of course their filtration efficiency entirely depends on their design and the fabric used.

Some currently available facemasks incorporate copper or silver ions. Interaction with a solid copper surface has been shown to inactivate virus particles after several hours. These facemasks are marketed as 'anti-microbial'. Any killing effect that is theoretically possible is only provided on contact with the metal, and the vast majority of the surface area of such masks does not incorporate an effective proportion of metal ions. Making these masks anti-viral using this approach would require adding a proportion of metal to the material that would make the mask both extremely uncomfortable to wear and prohibitively expensive. Consequently, this solution is impractical.

(III) What are the Shortcomings/Disadvantages of the Current Solutions?

A universal issue with masks is correct fit. Loose-fitting face-coverings of any kind aren't air tight and don't make the wearer impervious to infection. Because the air has to pass through an area of high resistance, the air is likely to try to find the path of least resistance and to find an unfiltered pathway, if such exists, letting in unfiltered air from the outside.

Another universal issue is the tendency of mask-wearers to touch, adjust, partially remove or fully remove the mask. Users do this because masks become uncomfortable, hot and moist and itchy. Adjusting the mask reduces any seal effect and allows air to flow directly round the mask into the mouth or nose. Additionally touching the mask transfers the concentrated particles from the outside of the mask to the fingers of the user, increasing the probability of introduction of an infectious dose to the user if they then touch their nose, mouth or eyes.

Disposable "surgical" facemasks are ill-fitting, and additionally, even when fitted in the best possible manner, will only filter out the largest particles and droplets. They certainly are helpful in reducing droplet spread from the wearer, but are fairly ineffective in reducing inhalation of droplets by the user. Importantly they do a good job of concentrating particles on their outside, increasing the probability of introduction of an infectious dose to the user if they then touch their nose, mouth or eyes.

N95 masks are much better at filtration, but again have the issues of proper fitting and of concentrating particles on their outside surface, thereby increasing the probability of introduction of an infectious dose to the user.

Reducing the pore size of disposable facemasks, so that they would remove smaller virus-containing droplets, would impact the ability of the wearer to breathe, encouraging removal or adjustment of the mask. This solution would therefore be counterproductive. And again, virus concentrated on the outside of the mask can act as an inoculum if touched and transferred to the wearer.

Copper and silver-containing anti-microbial facemasks currently being produced reduce growth of bacteria and fungi in the mask material, thereby reducing odors and extending the length of time an individual mask can be worn. However there are many disadvantages to these masks. The killing effect is only provided on contact with the metal, and the vast majority of the surface area of such masks does not incorporate an effective proportion of metal atoms/ions. Making these masks anti-viral using this approach would require adding a proportion of metal to the material that would make the mask both extremely uncomfortable to wear and prohibitively expensive. Consequently, this solution is impractical.

(IV) What is the New Solution and how does it Address the Current Problems?

The surface of enveloped viruses, such as SARS-CoV-2, is composed of lipids and proteins. Both types of biological material are susceptible to attack by enzymes. Lipids are degraded by lipases while proteins are degraded by proteases.

The surfaces of non-enveloped viral particles are composed of proteins and glycoproteins, which are likewise susceptible to degradation by the enzymes disclosed in the present invention.

The laundry detergent industry has for many years incorporated biological enzymes into dry laundry powders and stain removers. The enzymes are activated by the addition of water.

We propose incorporating proteases and lipases into the material of disposable facemasks to enhance their ability to prevent viral infections including those caused by influenza viruses and Coronaviruses such as Covid-19.

Proteases used in detergents are generally non-specific serine endoproteases that cleave on the hydroxyl-side of the hydrophobic amino acid residue. These enzymes are non-specific in that they are capable of hydrolyzing most peptide links.

Other proteases, not currently used in detergents (e.g. thiol proteases or metalloproteases), may also prove useful in anti-viral facemasks.

Lipases catalyze the hydrolysis of lipids. Lipases are a subclass of the esterases. Most lipases act at a specific position on the glycerol backbone of a lipid substrate. Common lipases convert triglyceride substrates to monoglycerides and two fatty acids.

Lipases used by the detergent industry have been selected based on their low substrate specificity and their stability in the presence of proteases.

Consequently, enzymes that have been selected for use in the detergent industry may prove ideal for incorporation into facemask material because they are broadly active, work at temperatures below body temperature, and are produced inexpensively in extremely large quantities. They have also been thoroughly tested for dermatologic tolerance.

Proteases, lipases and other enzymes which may be used in the present invention are listed in the paper by Hasan et al., *Enzymes used in detergents* August 2010 AFRICAN JOURNAL OF BIOTECHNOLOGY 9(31) which is hereby incorporated by reference for all purposes.

The enzymes present in these new anti-viral facemasks are activated when droplets of water touch the facemask material. The enzymes are solubilized under these conditions and move throughout the droplets.

This enzymatic anti-viral approach is superior to using metals in facemasks because of this solubility effect. Additional advantages are those of effectiveness and cost. The enzymes work extremely quickly and do not require hours of exposure, unlike copper/silver impregnation. The enzyme-impregnated mask is both easy to manufacture and cheaper to produce than the metal-impregnated design.

To the inventors' knowledge, detergent-industry enzymes have never been incorporated into facemasks, or other materials, to make use of their anti-viral properties. This approach to improving the efficiency of facemasks to prevent the spread of diseases, such as Covid-19, is consequently totally novel.

Enzyme-impregnated masks are suitable for the prevention and reduction in transmission of any viral respiratory diseases. These include (non-exclusively): influenza, the common cold, respiratory syncytial vim s infection, adenovirus infection, parainfluenza virus infection, severe acute respiratory syndrome (SARS) and Covid19.

Other embodiments are not limited to masks, but encompass all fabrics and related materials that are impregnated with or sprayed with enzymes that have anti-viral, anti-bacterial, or anti-microbial activity. The invention includes fabrics that are impregnated with or sprayed with proteases and/or lipases.

In one embodiment, the invention encompasses fabrics and similar materials that are impregnated with or sprayed with proteases only.

In one embodiment, the invention encompasses fabrics and similar materials that are impregnated with or sprayed with lipases only.

In one embodiment, the invention encompasses fabrics and similar materials that are impregnated with or sprayed with both proteases and lipases.

Figure 4:
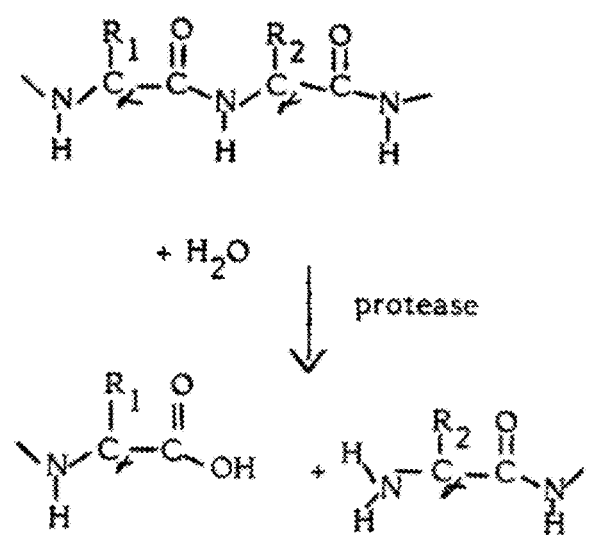
FIG. 4. Schematic action of a protease.

In general embodiments, the proteases used in the invention are non-specific serine endoproteases. These are capable of hydrolyzing most peptide links (FIG. 4).

The proteases used in the invention generally have low substrate specificity, work well at room temperatures, and are stable in the presence of lipases. Many commercial proteases are known that work at low temperature. See D. Kumar et al., 2008. *Microbial Proteases and Application as Laundry Detergent Additive*. Research Journal of Microbiology, 3: 661-672, incorporated by reference herein for all purposes.

Proteases used in the invention may include, alone or in combination, Serine proteases, Cysteine proteases, Aspartic proteases and Metalloproteases.

In other embodiments, proteases are thiol proteases or metalloproteases may be used.

In other embodiments, proteases may be, for example (non-exclusively) endoproteases or exoproteases, cutting at any amino acid at any location, and may be specific or non-specific in their action. A typical example used in the invention is a serine endoproteases.

Other embodiments may employ proteases selected from one or more of (alone or in any combination) Trypsin, Chymotrypsin, Endoproteinase Asp-N, Endoproteinase Arg-C, Endoproteinase Glu-C, Endoproteinase Lys-C, Thermolysin, Elastase, Papain, Proteinase K, Subtilisin, Clostripain, Exopeptidase, Carboxypeptidase A, Carboxypeptidase P, Carboxypeptidase Y, Cathepsin C, Acylamino-acid-releasing enzyme, and Pyroglutamate aminopeptidase.

Figure 3:
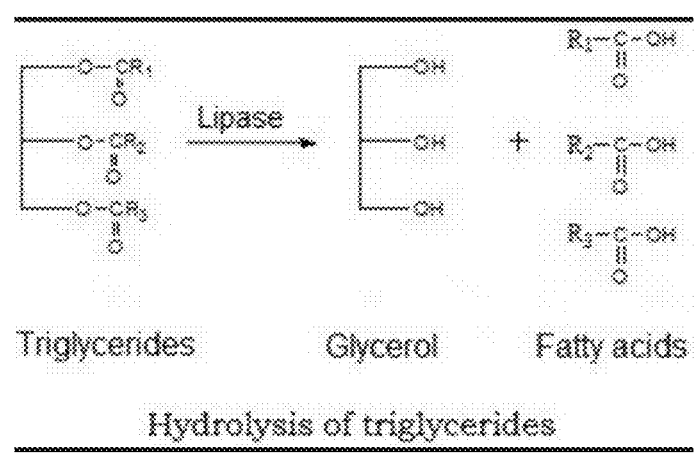
FIG. 3. Schematic action of a lipase.

Lipases, in general embodiments of the invention, act as esterases (FIG. 3). In general embodiments, the lipases used in the invention have low substrate specificity, work well at room temperatures and are stable in the presence of proteases.

In general embodiments, the lipases convert triglyceride substrates to monoglycerides and two fatty acids.

Lipases used in the invention will generally need to be active at lower temperatures, such as room temperature, between 10 and 25 degrees Centigrade. Cold active lipases (CLPs) are preferably used because they exhibit high catalytic activity at low temperatures. Since they are active at low temperatures consume less energy and also stabilize fragile compounds in the reaction medium. CLPs are commonly obtained from psychrophilic microorganisms which thrive in cold habitats. CLPs include *C. antarctica* lipase-A and *C. antarctica* lipase-B from *Candida antarctica* isolated from Antarctic organisms. These are well studied and industrially employed. See *Cold active lipases—an update*, M. Kavitha Frontiers in Life Science, 2016 VOL. 9, NO. 3, 226-238, incorporated herein by reference for all purposes.

Other embodiments, lipases may be, for example (non-exclusively), Lipolase (Novo Nordisk, Denmark), Lumafast (Genencore, USA), or Lipofast (Advanced Biochemicals, India).

Various lipases that are used in detergents and may be used in the present invention are discussed in D'Souza N M, Mawson A J (2005). "Membrane cleaning in the dairy industry: A review. Crit. Rev. Food Sci. Nutr. 45: 125-13.

Efficiency of the invention is measured in terms of inactivation of the virus over time in a controlled experiment. A standard measureable value of inactivation is $>T_{90}$ which is defined as the time for at least 90% inactivation of the viral population (measured as PFUs) in a controlled assay. In the present disclosure, the invention in the form of a paper fabric surgical mask impregnated with proteases and lipases, and sprayed with a viral load from an atomizing spray bottle, has a $>T_{90}$ of about 3 minutes. $T_{90}$ can be between 30 seconds and 30 minutes depending on various factors such as the moisture of the mask and the viral load distributed onto the mask surface, preferably from 1 minute to 15 minutes under experimental conditions. It is believed that, under constant atmospheric humidity, the longer the mask is worn, the greater the moisture in the mask will be, and therefore the faster the solubilization of the enzymes. However, viral particles will inherently be carried in water droplets, which should provide a suitable environment for enzyme solubilization as soon as the droplet contacts the fabric.

$T_{90}$ can be measured using the non-pathogenic enveloped bacteriophage Phi6 ($\phi$6) as a surrogate for enveloped waterborne viruses. Experientially, a solution of $\phi$6 is sprayed onto a test mask from a distance of 10 cm at a total spray volume of 0.5 ml, and at a $\phi$6 viral concentration of $10^4$ to $10^5$ plaque forming units per ml (PFUs/ml), with humidity maintained at 55% and temperature maintained at 23 degrees Centigrade. Samples are taken at various times and plaque formation is measured over time.

See Whitworth et al AEM Accepted Manuscript Posted Online 26 Jun. 2020 Appl. Environ. Microbiol. doi:10.1128/AEM.01482-20; and Nathalia Aquino de Carvalho et al., Evaluation of Phi6 Persistence and Suitability as an Enveloped Virus Surrogate Environ. Sci. Technol. 2017, 51, 15, 8692-8700; and Baize et al., Emergence of Zaire Ebola Virus Disease in Guinea N. Engl. J. Med. 2014, 371 (15) 1418-1425; all of which are incorporated by reference herein for all purposes.

In alternate embodiments, the invention may provide an inactivation efficiency of $>T_{70}$ (time to >70% inactivation measured by reduction in PFUs) of about 3 minutes. $T_{70}$ can be between 30 seconds and 60 minutes depending on various factors such as the moisture of the mask and the viral load distributed onto the mask surface. Preferably $T_{70}$ (or above) will be achieved between 1 min and 20 mins under standard conditions. Standard conditions are, for example, spraying a solution of $\phi$6 onto a test mask from a distance of 10 cm at a total spray volume of 0.5 ml, and at a $\phi$6 viral concentration of $10^4$ to $10^5$ plaque forming units per ml (PFUs/ml), with humidity maintained at 55% and temperature maintained at 23 degrees Centigrade.

In another alternate embodiments, the invention may provide an inactivation efficiency of $>T_{90}$ of about 1-20 mins, preferably 3-7 mins. In another alternate embodiments, the invention may provide an inactivation efficiency of $>T_{90}$ of 10-60 mins. In another alternate embodiments, the invention may provide an inactivation efficiency of $>T_{70}$ of 3-7 mins. In another alternate embodiments, the invention may provide an inactivation efficiency of $>T_{50}$ of 3-7 mins.

The fabric/mask of the invention does not have to achieve any specific inactivation efficiency with any particular virus, and any of these disclosed efficiencies will be sufficient to provide an effective reduction in viral infectivity. For example a 50% reduction over a period of an hour will significantly reduce the potential infective potential of a mask if left overnight.

It should be noted that since the enzymes are activated by an aqueous environment, lightly misting the mask after use (or during use) will enhance enzyme activation and increase efficiency of pathogen inactivation.

Advantages Over Metal-Containing Masks

Figure 6:
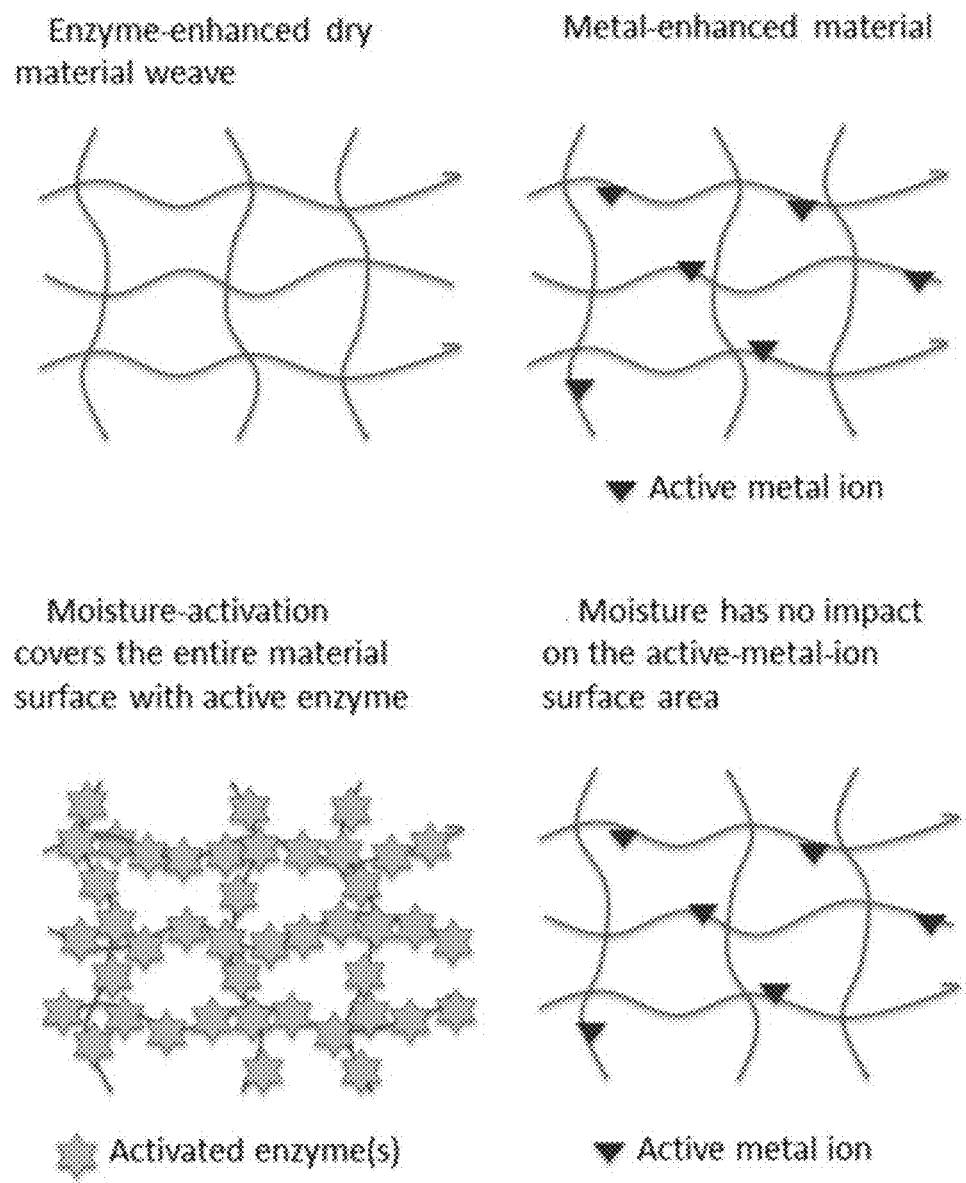
FIG. 6. Schematic diagram showing how moisture activates the enzymes over the entire surface area of the enzyme-enhanced materials, while having no effect on the active surface area of metal-enhanced materials.
Figure 7:
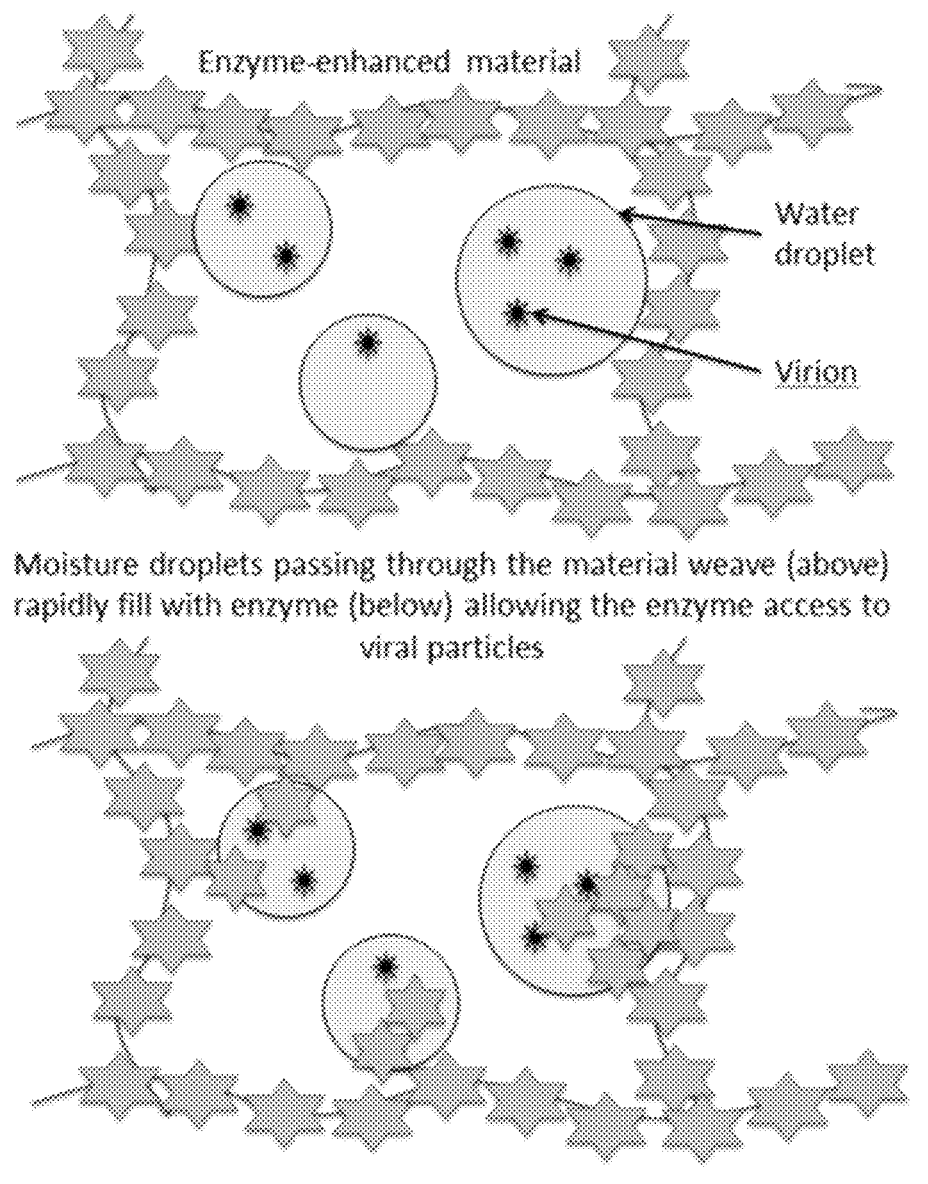

The present invention has particular advantages over metal-containing masks (see FIGS. 6 and 7).

Moisture activates the enzymes over the entire surface area of the enzyme-enhanced materials, while having no effect on the active surface area of metal-enhanced materials.

Activated enzymes disperse into aerosol droplets introduced into the face mask material during breathing (or sneezing, coughing, laughing, etc.)

Embodiments of the Invention

The invention provides fabrics that incorporate enzymes that inactivate viral particles, particularly enveloped viral particles such as those of Influenza virus and Coronavirus (e.g. Covid-19). The fabrics of the invention may be used in the production of various items including protective face-masks.

The fabrics of the invention work to inactivate not only viruses, but any microorganism that comes in contact with them that is susceptible to proteases and lipases or other relevant enzymes. Thus the invention is well suited to the inactivation of any organism that may come in contact with them. The fabrics of the invention may be used to inactivate not only organisms transmitted by droplets, but any organism that comes in contact with the fabrics of the invention such that enzymes are solubilized in an aqueous (or micro-aqueous) solution.

The enzymes may be incorporated into a fabric by impregnating, spraying or soaking the fabric with a solution containing the enzyme(s).

Fabrics include all spun or woven (or non-woven) or knitted, printed or pulped-and-dried materials regardless of flexibility or plasticity; for example, fabrics include (non-exclusively) all forms of paper fabric, cotton, wool, jute, hessian, linen, silk as well as man-made fabrics such as polyester, rayon, carbon fiber etc. and blends of man-made and natural materials.

Enzymes incorporated into the fabric include proteases and lipases. Proteases are generally non-specific proteases, cutting any amino acid at any location, being either endo-proteases or exoproteases. A typical example of a protease used in the invention is a serine endoprotease. Any lipase may be used such as Cold active lipases.

The enzymes of the present invention must be functionally active at room temperature at or below 15° C. to 25° C., preferable between 17° C. to 23° C. The degree of efficiency in use, at these temperatures provides an inactivation value $T_{90}$ between 30 seconds and 30 minutes, more specifically between 30 seconds and 5 minutes. Such a $T_{90}$ can be measured using the non-pathogenic enveloped bacteriophage Phi6 ($\phi$6) as a surrogate for enveloped waterborne viruses.

The invention provides fabrics that incorporate enzymes that inactivate pathogens such as viral particles or any type of microorganism susceptible to the enzymes used. The target pathogens are inactivated upon contact with the fabric in the presence of moisture, which solubilizes the enzymes and makes them active. Moisture is generally provided by the fluid in which the pathogens are suspended. This may be aqueous particles exhales from the respiratory system or coughed or sneezed out via the lungs, larynx, pharynx or indeed derived from and expelled from the esophagus. The moisture may also be provided by any pathogen-containing body fluids such as blood, serum, sputum or any other fluid from any animal or indeed any plant.

As mentioned previously, the invention is capable of being used to inactivate not only organisms transmitted by droplets, but any organism that comes in contact with the fabrics of the invention such that enzymes are solubilized in an aqueous (or micro-aqueous) solution.

Target organisms may include airborne organisms spread by droplet transmission such as coronaviruses and influenza, *legionella*, mycobacteria etc. It may include organisms responsible for Pneumonia, such as bacteria or viruses, and less commonly fungi and parasites. Pneumonia-causing bacteria most commonly (50% of cases) include *Streptococcus pneumonia*, but also include *Haemophilus* influenza (20%) *Chlamydophila pneumoniae* (13%) and *Mycoplasma pneumoniae* (3%), *Staphylococcus aureus, Moraxella catarrhalis*, and *Legionella pneumophila*.

Viruses that would be susceptible to the invention include, for example, rhinoviruses, coronaviruses, influenza virus, respiratory syncytial virus (RSV), adenovirus, and parainfluenza viruses.

Fungi that would be susceptible to the invention include, for example, *Histoplasma capsulatum, Blastomyces, Cryptococcus neoformans, Pneumocystis jiroveci* (*Pneumocystis pneumonia*, or PCP), and *Coccidioides immitis*.

Parasites that would be susceptible to the invention include, for example, *Toxoplasma gondii, Strongyloides stercoralis, Ascaris lumbricoides*, and *Plasmodium malariae*. These organisms typically enter the body through direct contact with the skin, ingestion, or via an insect vector. Except for *Paragonimus westermani*, most parasites do not specifically affect the lungs but involve the lungs secondarily to other sites.

Embodiments include all fabrics and uses of fabrics that may be used in a hospital or healthcare setting or a domestic setting where reduction in transmission pathogens is desirable. The invention is particularly well suited to producing disposable, single-use, anti-microbial fabrics, such as woven (or non-woven) paper fabrics for use as masks, paper tissues, bed clothes, pillowcases, curtains, gowns, clothes, head-coverings, surgical-ware, napkins, sanitary and absorbent coverings etc. and disposable clothes used in food-production and food-processing and in animal husbandry and agricultural processing settings.

Embodiments also include all fabric filters. Filters include those used for any purpose including filtering air, water, and any liquid or fluid. Filters may be used in air handling and air conditioning and air filtration systems. Filters may be used in air filtration systems in buildings and in cars, trains, airplanes and other vehicles.

The fabrics have the additional advantage of being incinerateable to produce no toxic byproducts, and also biodegradable. Additionally they may be made from recycled paper pulp. Additionally they have the advantage of being very easy and inexpensive to produce since all the components are readily available in every continent, and cheap and easy to produce.

Figure 5:
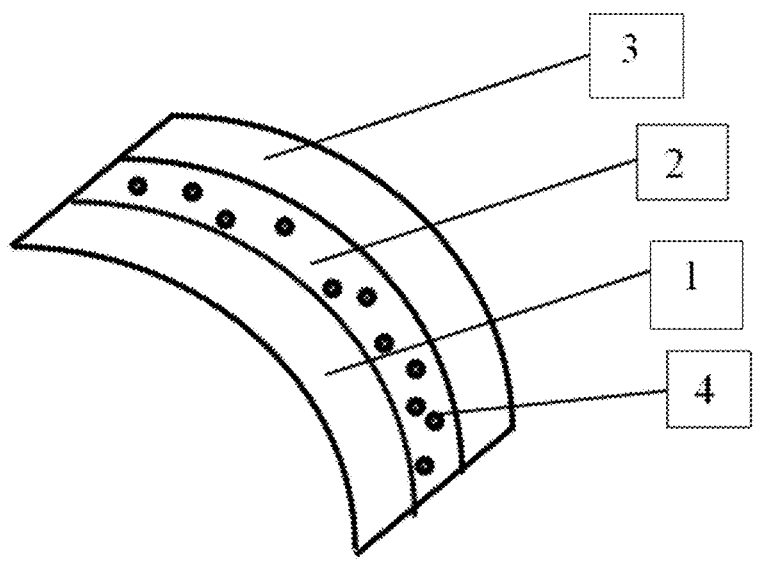
FIG. 5. Schematic diagram of an embodiment of the invention comprising three layers of fabric, as used in a face-mask, 1=inner layer nearest to user's face; 2=middle layer impregnated with enzymes; 3=outer layer with greater porosity than second layer; 4=enzymes incorporated into fabric.

Most of the embodiments above disclose fabrics/masks in which the enzymes are either distributed within the fabric or sprayed onto the fabric, and we do not mention the layered structure of the mask material. However, many masks are made of more than two layers of paper (typically three layers; FIG. 5). In certain embodiments, in use, (that is to say in the manufactured item), the items made from the materials comprise at least two layers. Sometimes all layers will comprise the enzyme(s).

Sometimes less than all layers will comprise the enzyme (s). This may be useful in an embodiment where it is desirable to keep the enzyme-impregnated layer away from the skin. For example, in a face mask made from 3 layers, only the middle layer may be enzyme-impregnated/sprayed such that the layer nearest the skin does not include enzymes. Or in a face mask made from 3 layers, or made from 2 layers, only the outer layer may be enzyme-impregnated/sprayed. This may be a preferred embodiment.

Or in another face mask made from 3 layers, only the middle layer may be enzyme-impregnated/sprayed. Three layers may be present and the outer layer may be more porous than the middle or inner layers. That is to say that the outer layer will allow larger particles to pass through than the middle layer or the inner layer. Droplets carrying pathogens will pass through the outer layer and be trapped in the enzyme-impregnated middle layer, and inactivated. This may be a preferred embodiment.

A specific commercial embodiment of the invention comprises a face mask comprising at least two layers of fabric, wherein only one layer of fabric is a fabric impregnated with enzymes, wherein the enzymes comprise proteases and lipases, wherein the enzymes are functionally active at a temperature between 17° C. to 23° C., and wherein, in use, the fabric impregnated with enzymes (the second layer) is separated from the face of the wearer by at least one other layer of fabric (the first layer) which is not impregnated with enzymes.

A preferred specific commercial embodiment of the invention comprises a face mask described above comprising three layers of fabric, wherein an outer layer (the third layer) is positioned on the outer surface of the second layer (the enzyme-impregnated layer) forming a permeable barrier between the environment and the second layer, and wherein the third layer is adapted to allow the free passage of larger diameter air-borne aqueous droplets than is the second layer, such that some air-borne aqueous droplets which pass through the third layer are adsorbed onto the second layer, such that the droplets, when adsorbed onto the second layer, solubilize and activate the enzymes in the second layer.

This last mask embodiment is particularly effective as it both traps and destroys viral pathogens while keeping them sequestered from the outer surface of the mask. This makes the masks more sanitary and more effective in use, and reduces the probability of user contamination.

A further embodiment specifically designs around other face-masks from the University of Kentucky (UK) that incorporate proteases that bind specifically to coronavirus spike proteins. There are several potential difficulties and disadvantages in the UK design. Firstly, these are enzymes that bind specifically to the spike-protein. These enzymes are not commercially available easily or cheaply or in large quantities. They must be created and manufactured by complex and expensive biological processes. This contrasts with the enzymes (proteases and lipases) of the present invention which have been developed over many years for use in washing detergents. They are cheap, well-researched and dermatologically tested. Secondly, the University of Kentucky mask, when in use, will not necessarily create an appropriate chemical and osmotic environment for the proteases to adopt the correct confirmation that will be required for enzyme activity. Thirdly the University of Kentucky (UK) mask only uses specific protease enzymes that bind only to the coronavirus spike protein. It does not employ non-specific enzymes, and it does not comprise lipases or other enzymes or multi-enzyme blends as does the present invention. Fourth, the enzymes used in the UK mask are not and have not been designed to be active at low temperatures, such as at room temperatures, for example 10-20 degrees centigrade. Therefore they will not function efficiently as room temperatures.

The prior art masks do not comprise non-specific or low specificity enzymes; they do not comprise enzymes designed to be active at low temperatures or enzymes that have the $T_{90}$ of the present invention. There is no reason to believe that a person could successfully use these prior art inventions to produce the invention of this disclosure (i.e., no expectation of success). They do not comprise a blend of low-temperature enzymes comprising proteases and lipases and the enzymes are not designed to be stable at low temperatures or in a dried form.

Some embodiments of the present invention specifically exclude certain types of enzymes, for example enzymes that bind specifically to the spike protein (or any other protein) of a coronavirus (or any other type of virus), but bind less well and with less specificity to most other proteins that do not have a structure similar to that of the spike protein. The embodiments of the invention comprise only non-specific or low-specificity enzymes. Such protease enzymes may bind at least as well to common proteins such as Casein as they do to a coronavirus spike protein.

For example the invention may specifically exclude enzymes that bind specifically to the spike protein of a coronavirus, but specifically include Serine proteases, Cysteine proteases, Aspartic proteases and/or Metalloproteases and also comprise Cold active lipases (CLPs), such as C. antarctica lipase-A and/or C. antarctica lipase-B from Candida Antarctica.

They may alternatively specifically exclude enzymes that bind specifically to the spike protein of a coronavirus, but specifically comprise Thiol proteases, metalloproteases, Trypsin, Chymotrypsin, Endoproteinase Asp-N, Endoproteinase Arg-C, Endoproteinase Glu-C, Endoproteinase Lys-C, Thermolysin, Elastase, Papain, Proteinase K, Subtilisin, Clostripain, Exopeptidase, Carboxypeptidase A, Carboxypeptidase P, Carboxypeptidase Y, Cathepsin C, Acylamino-acid-releasing enzyme, and Pyroglutamate aminopeptidase.

Methods of Preparation

Any type of fabric may be used in the invention, but a preferred embodiment uses paper-based fabrics. The paper-based fabrics of the invention employ simple and well-known techniques to produce woven and non-woven materials. Enzymes may be incorporated into the fabrics by simple means of adding enzymes to the pulping or washing phases of manufacture, prior to the dewatering phase.

Since the proteases and lipases are water-soluble, they will easily dissolve in the pulping or washing solution and will become evenly distributed within the paper pulp. The same applies to any weaving stage, if appropriate, where the solubilized enzymes will become evenly distributed within the fabric strands.

Since the proteases and lipases are highly stable, they can be dried, and enzyme-impregnated fabrics can be dewatered, and yet the enzymes will maintain their ability to perform their catalytic functions when exposed to an aqueous environment. In many practical instances, this will be a micro-aqueous environment created by an exhaled droplet contacting the fabric.

One important manufacturing issue is temperature. At high temperatures, the enzymes may become permanently denatured. Therefore it is important to avoid high temperatures, or even sustained moderate temperatures, during manufacture. In the present disclosure, high temperatures are those of 60° C. and above. In the present disclosure, moderate temperatures are those of 40° C. to 60° C. During the manufacturing process, the enzymes should not be exposed to temperatures above 45° C.

The concentration of enzymes in the pulp/wash solution can be determined empirically according to the enzyme being used. Because the enzymes are very inexpensive, cost is not a significant issue. A typical concentration in the wash solution for Serine proteases is 20 mg/ml. In other embodiments the concentration may be from 1000 mg/ml to 5 mg/ml. In the current manufacturing process, the pulp/wash solution can be recovered and reused for continuous manufacture of enzyme-enhanced paper-based fabrics. Similar concentrations can be used with lipase solutions.

In another embodiment, a protease and/or lipase solution can be sprayed onto a fabric of any kind, and subsequently dried. A typical concentration in the spray solution for proteases and/or lipases is 20 mg/ml. This should provide sufficient coverage to create a fabric with desirable viral inactivation efficiency, with a $T_{90}$ can be between 30 seconds and 60 minutes. Other concentration may be from 5 mg/ml to 1000 mg/ml.

The fabrics may be woven, or non-woven. The dried fabrics incorporating (or coated with) the enzymes may be cut, shaped and structured into various dimensions and shapes as required, such as into the form of a face mask.

Terms and Definitions

In the present disclosure, we may discuss enzyme activity. This can be confusing since there are several units of enzyme activity commonly in use. In this disclosure enzyme activity may be expressed using katal (symbol: kat) which is the catalytic activity that will raise the rate of reaction by one mole per second in a specified assay system. The katal is used to express catalytic activity, which is defined by the increase in the rate of reaction in an assay system. It is not used to express rates of reaction themselves which are expressed in mol/$s^{-1}$. Commonly, however, enzymatic activity is normally described as µmol/min (the number of µmol of substrate converted per minute). See Eur. J. Biochem. Y7, 319-320 (1979) Nomenclature Committee of the International Union of Biochemistry (NC-IUB) Units of Enzyme Activity Recommendations 1978. On the other hand, a more useful and practical measure of the efficiency of the fabrics of the invention is the inactivation efficiency, expressed as, for example, $T_{90}$, the time required to inactivate 90% of the pathogens, for example reducing PFUs by 90%. $T_{90}$ can be measured using the non-pathogenic enveloped bacteriophage Phi6 ($\phi$6) as a surrogate for enveloped waterborne viruses. Experimentally, a solution of $\phi$6 is sprayed onto a test mask from a distance of 10 cm at a total spray volume of 0.5 ml, and at a $\phi$6 viral concentration of $10^4$ to $10^5$ plaque forming units per ml (PFUs/ml), with humidity maintained at 55% and temperature maintained at 23° C.

Room temperature as used herein is from 12° C. to 30° C., more preferably from 17° C. to 25° C., more preferably from 17° C. to 22° C.

Proteases catalyze the breakdown of proteins into smaller polypeptides or amino acids by cleaving peptide bonds by hydrolysis.

Lipases catalyze the hydrolysis of lipids and are a subclass of the esterases.

Amylases catalyze the hydrolysis of starch into sugars.

Cellulases catalyze the decomposition of cellulose into simpler sugars.

Fabrics in this disclosure include any materials that can be formed into flexible sheets capable of being made into clothes sheets and the like.

Impregnated, in the present disclosure, refers to a substance that is incorporated into and throughout a substrate; when this word is used, the term 'sprayed' is inherently implied unless specifically excluded.

Sprayed, in the present disclosure, refers to a substance that is deposited onto a surface, and where used can equally be substituted with the action of painting, dipping or any other method to apply a substance onto a surface.

Virus/virion, in the present disclosure, refers to an obligate parasite without independent metabolism outside the host cell.

Inactivate, in the present disclosure, refers to the substantial reduction or elimination of the ability of an organism (including a virus) to reproduce.

Mask, in the present disclosure, refers to any face-covering designed to restrict or prevent the flow of particulate matter from the environment into the respiratory system of an animal. The disclosure is not limited to masks and applies to worn fabrics, filters etc.

A paper-based fabric, in the present disclosure, refers to any fabric made from at least 50% paper or lignin material, preferably 60%, 75%, 80%, 90% or at least 95% paper or lignin material.

The word manufactured, in the present disclosure, means made, constructed, or in any way confected.

REFERENCES

The following references and any mentioned in this disclosure are hereby incorporated by reference in their entirety for all purposes.

Niyonzima et al., Coproduction of detergent compatible bacterial enzymes and stain removal evaluation. J. Basic Microbiol. 2015 October; 55(10):1149-58.

Niyonzima et al., Detergent-compatible bacterial cellulases. FN. J Basic Microbiol. 2019 February; 59(2):134-147.

Niyonzima et al., Detergent-compatible bacterial amylases. Appl Biochem Biotechnol. 2014 October; 174(4):1215-1232.

Haddar A, et al., Two detergent stable alkaline serine-proteases from *Bacillus mojavensis* A21: purification, characterization and potential application as a laundry detergent additive. Bioresour Technol. 2009 July; 100 (13):3366-73.

Chen B. Y, et al., Utility of enzymes from *Fibrobacter succinogenes* and *Prevotella ruminicola* as detergent additives. J. Ind Microbiol Biotechnol. 2008 August; 35(8):923-30.

D'Souza N. M, et al., Membrane cleaning in the dairy industry: A review. Crit. Rev. Food Sci. Nutr. 45: 125-13, 2005.

M. Kavitha et al., Cold active lipases, an update, Frontiers in Life Science, 2016 VOL. 9, NO. 3, 226-238.

Whitworth et al., AEM Accepted Manuscript Posted Online 26 Jun. 2020 Appl. Environ. Microbiol.

Nathalia Aquino de Carvalho et al., Evaluation of Phi6 Persistence and Suitability as an Enveloped Virus Surrogate Environ. Sci. Technol. 2017, 51, 15, 8692-8700.

Baize et al., Emergence of Zaire Ebola Virus Disease in Guinea N. Engl. J. Med., 371 (15) 1418-1425, 2014.

Eur. J. Biochem. Y7, 319-320 (1979) Nomenclature Committee of the International Union of Biochemistry (NC-IUB) Units of Enzyme Activity Recommendations 1978

The invention claimed is:

1. A disposable face mask which when worn, covers the nose and mouth of a wearer, comprising at least two layers of fabric, wherein one layer of fabric has enzymes incorporated within it, wherein the enzymes explicitly exclude enzymes that bind specifically to the spike protein of a coronavirus, and comprise low-temperature proteases and low-temperature lipases which enzymes are functionally active at a temperature between 17° C. to 23° C., and wherein, the fabric layer that has enzymes incorporated within it is separated from the face of the wearer by at least one other layer of fabric that does not have enzymes incorporated within it, wherein the enzymes inactivate enveloped viruses carried in an aqueous droplet, upon contact with the fabric, wherein the inactivation time $T_{75}$ is less than 30 minutes.

2. A method for excluding airborne pathogens from the respiratory tract of a subject, the method comprising:
  (i) providing a subject desirous of excluding airborne pathogens from the subject's respiratory tract;
  (ii) providing a disposable face mask, the face mask comprising: at least two layers of fabric, wherein one layer of fabric has enzymes incorporated within it, wherein the enzymes explicitly exclude enzymes that bind specifically to the spike protein of a coronavirus, and wherein the enzymes comprise low-temperature proteases and low-temperature lipases that are functionally active at a temperature between 17° C. to 23° C., and wherein, the fabric layer that has enzymes incorporated within it is separated from the face of the wearer by at least one other layer of fabric that does not have enzymes incorporated within it, wherein the enzymes inactivate enveloped viruses carried in an aqueous droplet, upon contact with the fabric, wherein the inactivation time $T_{75}$ is less than 30 minutes,
  (iii) fitting the face mask to the face of the subject such that the mouth and nose of the subject are covered such that inhaled air passes through the fabric of the mask into the subject's respiratory tract, such that airborne pathogens are excluded from the respiratory tract of a subject.

3. The disposable face mask of claim 1 wherein the inactivation time $T_{75}$ is less than 15 minutes.

4. The disposable face mask of claim 1 wherein the proteases comprise a non-specific serine protease, stable and active in the presence of lipases, and the lipases are stable and active in the presence of proteases and are functionally active at a temperature between 17° C. to 23° C. and wherein the inactivation value $T_{75}$ is less than 30 minutes.

5. The disposable face mask of claim 1, wherein the proteases comprise at least one of Serine proteases, Cysteine proteases, Aspartic proteases and Metalloproteases, Thiol proteases, metalloproteases, Trypsin, Chymotrypsin, Endoproteinase Asp-N, Endoproteinase Arg-C, Endoproteinase Glu-C, Endoproteinase Lys-C, Thermolysin, Elastase, Papain, Proteinase K, Subtilisin, Clostripain, Exopeptidase, Carboxypeptidase A, Carboxypeptidase P, Carboxypeptidase Y, Cathepsin C, Acylamino-acid-releasing enzyme, and Pyroglutamate aminopeptidase.

6. The disposable face mask of claim 1, wherein the lipases comprise Cold active lipases (CLPs).

* * * * *